(12) United States Patent
Yonezawa et al.

(10) Patent No.: US 9,851,318 B2
(45) Date of Patent: Dec. 26, 2017

(54) METHOD OF DETECTING AIR GAP IN GYPSUM-BASED BUILDING BOARD AND METHOD OF MANUFACTURING GYPSUM-BASED BUILDING BOARD

(71) Applicant: YOSHINO GYPSUM CO., LTD., Tokyo (JP)

(72) Inventors: Shinji Yonezawa, Tokyo (JP); Yasutoshi Ueno, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 368 days.

(21) Appl. No.: 14/434,427

(22) PCT Filed: Jun. 17, 2013

(86) PCT No.: PCT/JP2013/066632
§ 371 (c)(1),
(2) Date: Apr. 9, 2015

(87) PCT Pub. No.: WO2014/061308
PCT Pub. Date: Apr. 24, 2014

(65) Prior Publication Data
US 2015/0268183 A1 Sep. 24, 2015

(30) Foreign Application Priority Data
Oct. 18, 2012 (JP) .................. 2012-230499

(51) Int. Cl.
*G01N 25/72* (2006.01)
*B28B 17/00* (2006.01)
(Continued)

(52) U.S. Cl.
CPC ......... *G01N 25/72* (2013.01); *B28B 17/0072* (2013.01); *B28B 19/0092* (2013.01); *G06T 7/0008* (2013.01); *G06T 2207/10004* (2013.01)

(58) Field of Classification Search
USPC ............................................. 374/5
See application file for complete search history.

(56) References Cited

U.S. PATENT DOCUMENTS 5,711,603 A * 1/1998 Ringermacher ....... G01N 25/72
374/124
6,418,638 B1 * 7/2002 Forster ................... B28B 11/24
156/39
(Continued)

FOREIGN PATENT DOCUMENTS

DE 19953415 7/2001
JP S59-196452 11/1984
(Continued)

OTHER PUBLICATIONS

Taiwanese Office Action dated Oct. 25, 2016.
International Search Report dated Aug. 13, 2013.
Extended European search report dated Aug. 7, 2015.

*Primary Examiner* — Clayton E Laballe
*Assistant Examiner* — Leon W Rhodes, Jr.
(74) *Attorney, Agent, or Firm* — IPUSA, PLLC

(57) ABSTRACT

A method of detecting an air gap in a gypsum-based building board includes cooling a surface of a gypsum-based building board that has generated heat because of a hydration reaction of calcined gypsum by applying a cooling medium to the surface, and detecting a temperature distribution of the surface of the gypsum-based building board after completion of the cooling.

3 Claims, 3 Drawing Sheets

(51) Int. Cl.
  *G06T 7/00*      (2017.01)
  *B28B 19/00*    (2006.01)

(56)           References Cited

U.S. PATENT DOCUMENTS 7,803,296 B2 *  9/2010  Miller .................... B28B 5/027
                                                                106/677
  8,506,159 B2 *  8/2013  Nakagawa ............. G01N 25/72
                                                                250/338.1
  2010/0074515 A1  3/2010  Zhao et al.

FOREIGN PATENT DOCUMENTS

| JP | 06003303 A | * | 1/1994 | ......... B28B 17/0072 |
| JP | H06-003303 | | 1/1994 | |
| JP | H10-278910 | | 10/1998 | |
| JP | H11-002611 | | 1/1999 | |
| JP | 2005-221395 | | 8/2005 | |
| JP | 2007-327755 | | 12/2007 | |
| WO | 01/35086 | | 5/2001 | |
| WO | 20101059728 | | 5/2010 | |

\* cited by examiner

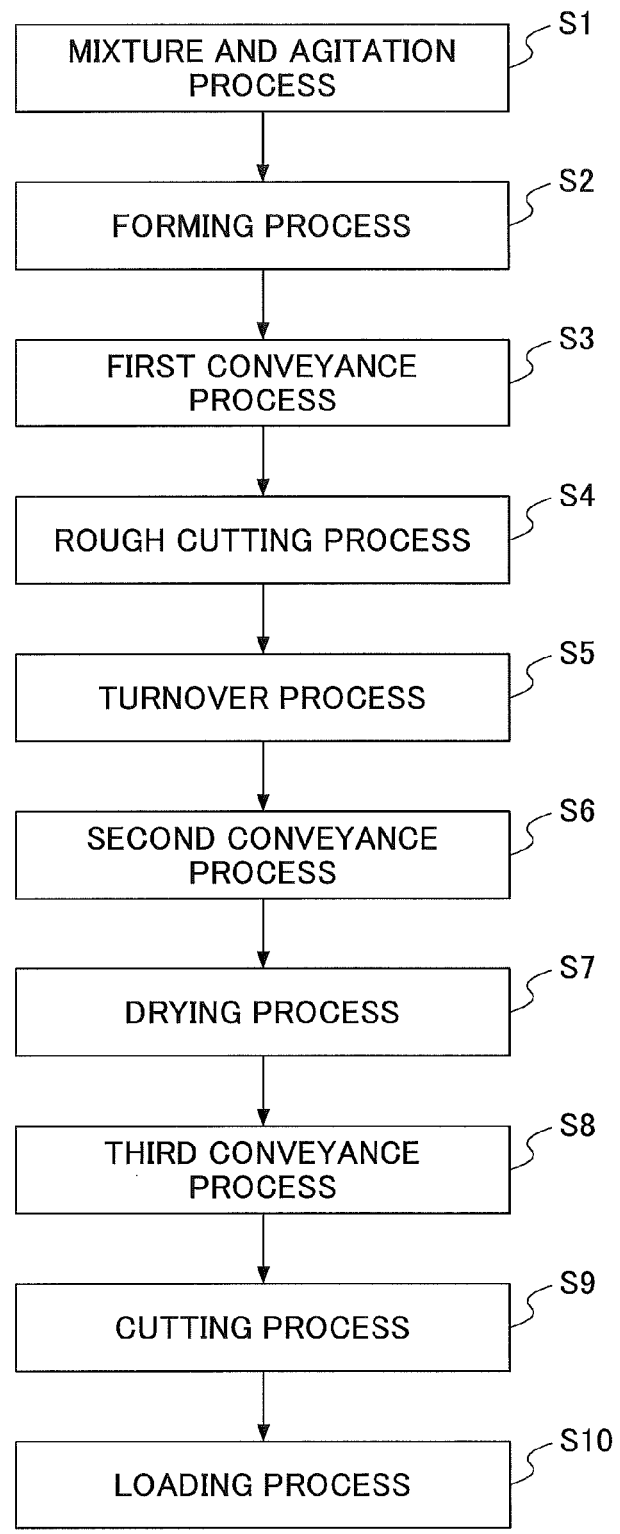

METHOD OF DETECTING AIR GAP IN GYPSUM-BASED BUILDING BOARD AND METHOD OF MANUFACTURING GYPSUM-BASED BUILDING BOARD

TECHNICAL FIELD

The present invention relates to methods of detecting an air gap in a gypsum-based building board and methods of manufacturing a gypsum-based building board.

BACKGROUND ART

Gypsum-based building boards are widely used as interior materials for building because of their inexpensiveness as well as their excellent characteristics such as fire prevention and fire-resisting performance, sound-insulating performance, heat-insulating performance, and workability. Examples of gypsum-based building boards include gypsum boards, fire-resistant gypsum boards, regular hard gypsum boards, gypsum boards containing glass fiber tissues, and glass mat gypsum boards.

In general, in addition to being uniform in thickness, width and length dimensions and having a predetermined strength, having a smooth surface without any exterior defects that are harmful in use, such as chips, cracks, contaminations, dents, and deflection, is desired of these gypsum-based building boards as an important quality. One of these defects detrimental to quality is air gaps or so-called captured air bubbles captured at the time of forming.

Captured air bubbles refer to air bubbles relatively large in size so as to be easily identifiable by human eyes, which are included in a gypsum core when a gypsum slurry hardens to form a product after passing through a forming machine with air captured inside when a material passes through the forming machine (upper paper, a gypsum slurry, and lower paper pass through the forming machine in the case of a gypsum board, for example) at the time of manufacture of a gypsum-based building board. Usually, captured air bubbles are spherical or ellipsoidal air bubbles (hereinafter referred to as "air gaps").

When an air gap is generated in a gypsum-based building board product, a depression or bulge is likely to appear on a surface of part of the product in which part the air gap is contained inside the core of the product. This prevents formation of a smooth surface and is thus not preferable in terms of quality.

Furthermore, in terms of quality, there is a problem in that it is not possible to fix the gypsum-based building board product by driving a nail or screw into the part containing the air gap because of the absence of gypsum, which is supposed to form the core.

Therefore, in general, in forming gypsum-based building boards, a pool of gypsum slurry is provided right in front of the entrance of the forming machine and various measures are taken to keep its retained amount constant.

It is difficult, however, to keep the amount of retained gypsum slurry constant because of variations in the quality or the amount of supply of a raw material and differences in the type of a manufactured product and manufacturing conditions. Therefore, there has been no solution so far to the generation of air gaps.

As a result, it is desired to detect and select generated air gaps with reliability. For example, gypsum board cover paper is present at the surface of a gypsum board and gypsum is present at the surface of a gypsum board containing glass fiber tissues. Therefore, the presence of air gaps cannot be visually confirmed unless a dent or bulge appears on the surface of the gypsum-based building board or except in a section of the board.

Therefore, there has been a demand for a method of detecting an air gap inside a gypsum-based building board without cutting or breaking the product.

Patent Document 1 discloses a method of manufacturing a sheet member, in which an optical image of a sheet is first detected and possible defects generated on a surface of or inside the sheet are detected from the optical image. Then, the possible defective parts of the sheet are exposed to infrared radiation or a cooling gas or heating gas is jetted to the possible defective parts of the sheet, and the kinds of defects are determined based on the temperature change characteristics of the possible defective parts in their state of heat generation due to the absorption of infrared radiation or based on the temperature change characteristics or the like of the possible defective parts in their state of heat radiation or the like, thereby grading and manufacturing sheets.

Patent Document 2 discloses a detector and a method for detecting a defective part of a sample, where the detector includes first means for heating or cooling a sample, second means for applying a thermal action reverse to that of the first means to the sample simultaneously with the heating or cooling by the first means, and infrared radiation detecting means for detecting infrared radiation from the sample during the simultaneous heating and cooling of the sample.

PRIOR ART DOCUMENTS

Patent Documents

[Patent Document 1] Japanese Laid-Open Patent Application No. 11-2611
[Patent Document 2] Japanese Laid-Open Patent Application No. 2007-327755

SUMMARY OF THE INVENTION

Problems to be Solved by the Invention

The above-described conventional techniques, however, require multiple processes to detect an air gap, so that there is a problem in that the detection takes time and effort and causes an increase in equipment size.

In view of the above-described conventional technical problems, the present invention has an object of providing a method of detecting an air gap in a gypsum-based building board that enables easy detection of an air gap inside a gypsum-based building board and is applicable to an initial process in a gypsum-based building board manufacturing process to enable early detection of an air gap.

Means for Solving the Problems

According to an aspect of the present invention, a method of detecting an air gap in a gypsum-based building board includes cooling a surface of the gypsum-based building board that has generated heat because of a hydration reaction of calcined gypsum by applying a cooling medium to the surface; and detecting a temperature distribution of the surface of the gypsum-based building board after completion of the cooling.

According to an aspect of the present invention, a method of manufacturing a gypsum-based building board includes forming a gypsum-based building board of the predetermined shape; cooling a surface of the gypsum-based building board that has generated heat because of a hydration reaction of calcined gypsum by applying a cooling medium to the surface; detecting a temperature distribution of the surface of the gypsum-based building board after completion of the cooling; imaging the temperature distribution obtained in the detecting; and detecting a size of an air gap contained in the gypsum-based building board by performing image processing on an image of the temperature distribution of the surface of the gypsum-based building board obtained in the imaging.

Effects of the Invention

According to an aspect of the present invention, an exothermic reaction due to the hydration of calcined gypsum in a gypsum-based building board is used. Accordingly, it is possible to omit the installation of equipment and heating energy for newly applying heat to a product. This makes it possible to easily detect an air gap in a gypsum-based building board.

Furthermore, a method of detecting an air gap in a gypsum-based building board according to this embodiment may be applied to an early process in a process for manufacturing a gypsum-based building board. Therefore, when a defective product containing an air gap larger than or equal to a predetermined size is generated, it is possible to detect the air gap in a short period of time after the generation and to provide feedback concerning the manufacturing conditions. As a result, it is possible to reduce the number of defective products and to improve a yield.

BRIEF DESCRIPTION OF THE DRAWINGS

FIG. 3 is a flowchart of the method of manufacturing a gypsum-based building board according to the second embodiment of the present invention.

DESCRIPTION OF EMBODIMENTS

Figure 1A:
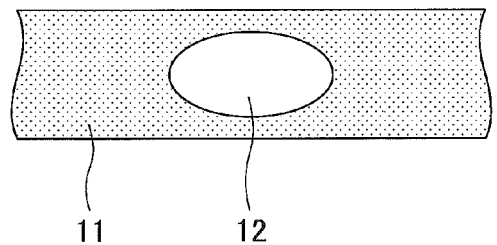
FIG. 1A is a diagram illustrating a method of detecting an air gap in a gypsum-based building board according to a first embodiment of the present invention.

A description is given below, with reference to the accompanying drawings, of embodiments of the present invention.

First Embodiment

A description is given of a method of detecting an air gap in a gypsum-based building board according to a first embodiment.

The method of detecting an air gap in a gypsum-based building board according to this embodiment includes a cooling process of cooling a surface of a gypsum-based building board that has generated heat because of the hydration reaction of calcined gypsum by applying a cooling medium to the surface, and a temperature distribution detection process of detecting a temperature distribution of the surface of the gypsum-based building board after completion of the cooling.

The gypsum-based building board to be measured may be, but is not limited in particular to, for example, a gypsum board, a fire-resistant gypsum board, a regular hard gypsum board, a gypsum board containing glass fiber tissues, or a glass mat gypsum board. The glass mat gypsum board referred to here is a gypsum board whose cover paper is replaced with glass mats.

As described below, the gypsum-based building board is manufactured by forming a gypsum slurry and, for example, cover paper, glass mats, or glass fiber tissues into a predetermined shape and thereafter subjecting the obtained formed product to a drying process, etc.

The gypsum slurry is obtained by agitating and mixing calcined gypsum and water, and an adhesive agent and other various kinds of additives as required, with a mixer agitator (main mixer).

Calcined gypsum, which is also referred to as a calcium sulfate hemihydrate, is an inorganic composition having a hydraulic property. As the calcined gypsum, β-type hemihydrate gypsum, which is obtained by calcining natural gypsum, by-product gypsum, desuflogypsum or the like, or any mixture gypsum thereof in the atmosphere, α-type hemihydrate gypsum, which is obtained by calcining natural gypsum, by-product gypsum, desuflogypsum or the like, or any mixture gypsum thereof in water, or a mixture of β-type hemihydrate gypsum and α-type hemihydrate gypsum may be used. Calcining in water includes calcining in vapor.

Examples of the adhesive agent may include known materials such as starch, polyvinyl alcohol, and carboxymethyl cellulose (CMC).

Examples of various kinds of additives may include various kinds of dispersants, hardening adjustors, waterproofing agents, reinforcing fibers, and lightweight aggregates.

Furthermore, a foam may be mixed into the gypsum slurry in order to reduce the weight of the gypsum-based building board. The foam referred to here means fine bubbles uniformly dispersed in an aqueous gypsum slurry used to manufacture the gypsum-based building board or in a gypsum core after the hardening of the aqueous gypsum slurry.

In injecting a foam, a foam is formed in advance by adding a foaming agent to water. Thereafter, the water to which the foaming agent is added is mixed with other materials of the gypsum slurry, and the obtained mixture is agitated. The foaming agent used at this point may be, but is not limited in particular to, for example, sodium alkyl sulfate, alkyl ether sulfate, sodium alkylbenzene sulfonate, and polyoxyethylene alkyl sulfate, which are used by way of being diluted to concentrations at which they are normally employed in general.

As described above, the gypsum slurry of the gypsum-based building board is manufactured by mixing calcined gypsum, water, etc., and the calcined gypsum generates heat of hydration when the calcined gypsum is hydrated to harden. The temperature of the gypsum-based building board at this point is approximately 35° C. to approximately 60° C.

Therefore, in the method of detecting an air gap in a gypsum-based building board according to this embodiment, a surface of a gypsum-based building board that has generated heat because of the hydration reaction of calcined gypsum is cooled by applying a cooling medium to the surface, and then a temperature distribution of the surface of the gypsum-based building board is detected.

Figure 1B:
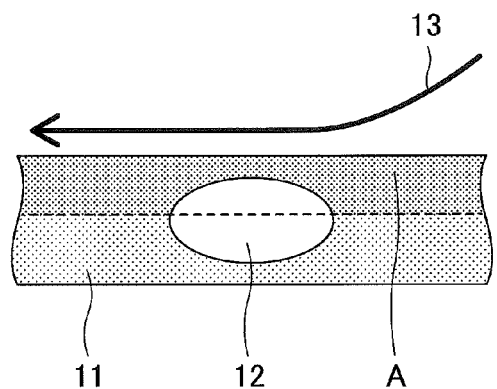
FIG. 1B is another diagram illustrating the method of detecting an air gap in a gypsum-based building board according to the first embodiment of the present invention.
Figure 1C:
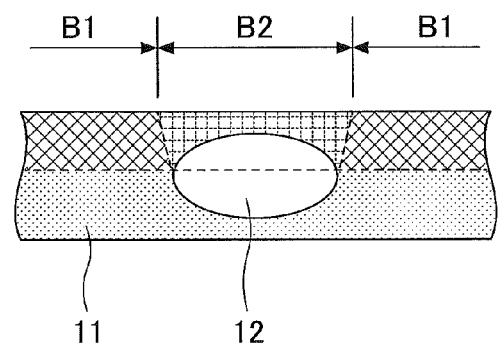
FIG. 1C is another diagram illustrating the method of detecting an air gap in a gypsum-based building board according to the first embodiment of the present invention.

A description is given of this point using FIGS. 1A, 1B, and 1C.

FIGS. 1A through 1C schematically illustrates cross-sectional views of an air gap and its periphery in the case where the air gap is contained in a gypsum-based building board. As described above, the gypsum-based building board includes cover paper, whose graphical representation is omitted in FIGS. 1A through 1C for convenience of description.

FIG. 1A illustrates a cross section of the gypsum-based building board having heat of hydration after completion of a forming process. Referring to FIG. 1A, an air gap 12 is contained in a gypsum slurry 11.

Then, as illustrated in FIG. 1B, a cooling medium is applied to a surface of the gypsum-based building board that has generated heat because of the hydration reaction of calcined gypsum, so that the surface is temporarily cooled. By thus applying a cooling medium to a surface of the gypsum-based building board, for example, a surface portion (a region formed of a surface and a portion of a certain depth under the surface) indicated by A of the gypsum-based building board is cooled. In the gypsum-based building board, the degree of cooling differs between a part containing an air gap and other parts. Therefore, a temperature distribution is caused by simply applying a cooling medium to a surface of the gypsum-based building board.

At this point, the temperature to which the surface portion of the gypsum-based is cooled is not limited, and cooling may be so performed as to enable detection of a temperature difference between a part containing the air gap (air bubble) 12 and other parts of the gypsum-based building board in a temperature distribution detection process to be described below. Therefore, it is preferable to supply a cooling medium so as to cause a temperature difference between the part containing the air gap (air bubble) 12 and other parts of the gypsum-based building board, for example, to cause the part containing the air gap (air bubble) 12 to be lower in temperature by approximately 3 to 5° C. than other parts of the gypsum-based building board, at the time of performing the temperature distribution detection process after applying the cooling medium to the surface of the gypsum-based building board.

The cooling medium is not limited in particular. Cooling media that do not affect the quality of the gypsum-based building board may be preferably used. For example, air or water may be preferably used. The amount, the rate of supply, and the temperature of the cooling medium at the time of supplying the cooling medium are not limited. For example, cooling may be performed so that the gypsum-based building board is cooled to the above-described degree (so as to cause a temperature difference between a part containing an air gap and other parts for a predetermined time after cooling) without losing its formed shape. The cooling medium may be supplied by causing a current of air with a blower or the like or spraying water using a spray.

The above-described cooling medium and its supplying method are not limited to these, and other cooling media and other supplying methods may also be used.

Next, as illustrated in FIG. 1C, the gypsum-based building board after completion of the cooling process illustrated in FIG. 1B still generates heat because of the hydration reaction. Therefore, the surface of a part B1 that does not contain an air gap rises back to its original temperature earlier than a part B2 that contains the air gap (air bubble) 12.

Therefore, the surface temperature difference of the gypsum-based building board between the part B2 that contains the air gap 12 and the other part B1 at the time when the temperature of the surface of the part B1 that contains no air gap has risen back to its original temperature because of heat generation due to the heat of hydration of calcined gypsum after the cooling process is more distinct than the surface temperature difference between a part that contains an air gap and other parts of the gypsum-based building board caused by the cooling process alone. That is, by performing the cooling process, a temperature distribution is caused at a surface of the gypsum-based building board in accordance with the internal gypsum density of the gypsum-based building board, and thereafter, the temperature of a part that contains no air gap increases because of the heat of hydration of calcined gypsum, so that the temperature distribution becomes clearer.

Therefore, by performing a temperature distribution detection process to detect the temperature distribution after completion of the cooling process, it is possible to detect a position at which an air gap (air bubble) is contained from the obtained temperature distribution of a surface of the gypsum-based building board.

In particular, when a region of a different temperature in the temperature distribution (a region corresponding to an air gap) exists over an area of a predetermined size or larger, such a region may be detected as an air gap that affects product quality.

A device that detects a temperature distribution (a temperature distribution detection device) is not limited in particular as long as the device is capable of detecting the temperature distribution of a surface of the gypsum-based building board to be measured. For example, thermography (an infrared camera) may be employed.

When the gypsum-based building board to be measured has a large area (width), the gypsum-based building board may be divided into multiple regions, and a temperature distribution may be detected region by region. At this point, multiple temperature distribution detection devices (such as infrared cameras) may be prepared and caused to perform measurement simultaneously, or one or more temperature distribution detection devices may be moved to perform measurement in each region.

Furthermore, a resolution of the temperature distribution detection device may be selected based on the size of a region of a different temperature in the temperature distribution (a region corresponding to an air gap) to be identified. For example, it is preferable that the temperature distribution detection device have such a resolution as to enable detection of a region of a different temperature in the temperature distribution (a region corresponding to an air gap) of 10 mm or larger in diameter, and it is more preferable that the temperature distribution detection device have such a resolution as to enable detection of a region of a different temperature in the temperature distribution (a region corresponding to an air gap) of 5 mm or larger in diameter. It is still more preferable that the temperature distribution detection device have such a resolution as to enable detection of a region of a different temperature in the temperature distribution (a region corresponding to an air gap) of 3 mm or larger in diameter, and it is particularly preferable that the temperature distribution detection device have such a resolution as to enable detection of a region of a different temperature in the temperature distribution (a region corresponding to an air gap) of 1 mm or larger in diameter.

The period before performing the temperature distribution detection process after the cooling process varies in accordance with the temperature attained in the cooling process, the composition of the gypsum slurry, etc., and is therefore not limited. The temperature distribution detection process may be performed after a temperature distribution corresponding to a part containing an air gap and other parts is caused at a surface of the gypsum-based building board by the cooling process. In particular, it is preferable that the temperature distribution detection process be performed after the temperature difference between a part containing an air gap and other parts becomes more distinct because of the heat of hydration of calcined gypsum as described above. The above-described temperature distribution of a surface of the gypsum-based building board does not have to reflect all air gaps in the gypsum-based building board, and may be satisfactory if reflecting at least air gaps (of a shape, size, etc.) to be detected.

Normally, with respect to a part that contains no air gap, the temperature of a surface of the gypsum-based building board immediately rises because of the heat of hydration of calcined gypsum after the cooling process. Therefore, it is possible to measure a temperature distribution substantially successively after completion of the cooling process.

Furthermore, it is preferable that the method of detecting an air gap in a gypsum-based building board according to this embodiment further include a temperature distribution imaging process of imaging the temperature distribution obtained in the temperature distribution detection process and an air gap size detection process of detecting the size of an air gap contained in the gypsum-based building board by performing image processing on the image of the temperature distribution of a surface of the gypsum-based building board obtained in the temperature distribution imaging process.

By performing the temperature distribution imaging process as described above, the temperature distribution of a surface of the gypsum-based building board may be obtained as an image. At this point, the form or format of the image is not limited in particular, and the image may be in any form or format that allows the image to be subjected to image processing in the air gap size detection process.

Furthermore, it is preferable to detect the size of an air gap contained in the gypsum-based building board by performing image processing on the obtained temperature distribution image.

By thus imaging and then performing image processing on the temperature distribution, it is possible to calculate a specific size of the air gap with accuracy. In particular, this is preferable in the case of application to an actual manufacturing process because detecting the size of an air gap by performing image processing makes it possible to perform processing without overlooking air gaps larger than or equal to a predetermined size.

In the air gap size detection process, it is possible to detect (calculate) the size of an air gap with respect to all regions of a different temperature in the temperature distribution that appears at a surface of the gypsum-based building board (all regions corresponding to air gaps). It is preferable, however, to detect the size of an air gap with respect to a region of a different temperature in the temperature distribution (a region corresponding to an air gap) which region is larger than or equal to a predetermined certain size.

For example, in the case of ejecting at least some of the manufactured products outside the system of a manufacturing process or changing manufacturing conditions based on a detected air gap size, the size of a region of a different temperature in the temperature distribution (a region corresponding to an air gap) to be subjected to an operation may be selected (determined) in view of detection accuracy, etc., so that an air gap of a size that serves as a reference for determination is detectable.

As has been described, according to the method of detecting an air gap in a gypsum-based building board of this embodiment, heat generation due to the heat of hydration (of the calcined gypsum) of a product (a gypsum-based building board) is used. Therefore, there is no need to newly apply heat, so that it is possible to omit equipment and energy for heat application.

Furthermore, a temperature difference is caused by simply cooling a surface of a product with a cooling medium. The temperature difference is more distinct because of the continuing heat generation of the product than a temperature difference caused by cooling alone, thus facilitating detection of an air gap inside the product.

Furthermore, the method of detecting an air gap in a gypsum-based building board of this embodiment may be applied to the upstream part of a process for manufacturing a gypsum-based building board to be described below. Therefore, even when a defective product that contains an air gap larger than or equal to a predetermined size is generated, it is possible to detect the defective product and provide feedback concerning the manufacturing conditions at an early stage, so that it is possible to reduce the number of defective products and to improve a yield.

Second Embodiment

In a second embodiment, a description is given of a method of manufacturing a gypsum-based building board including the method of detecting an air gap in a gypsum-based building board described in the first embodiment.

Figure 2:
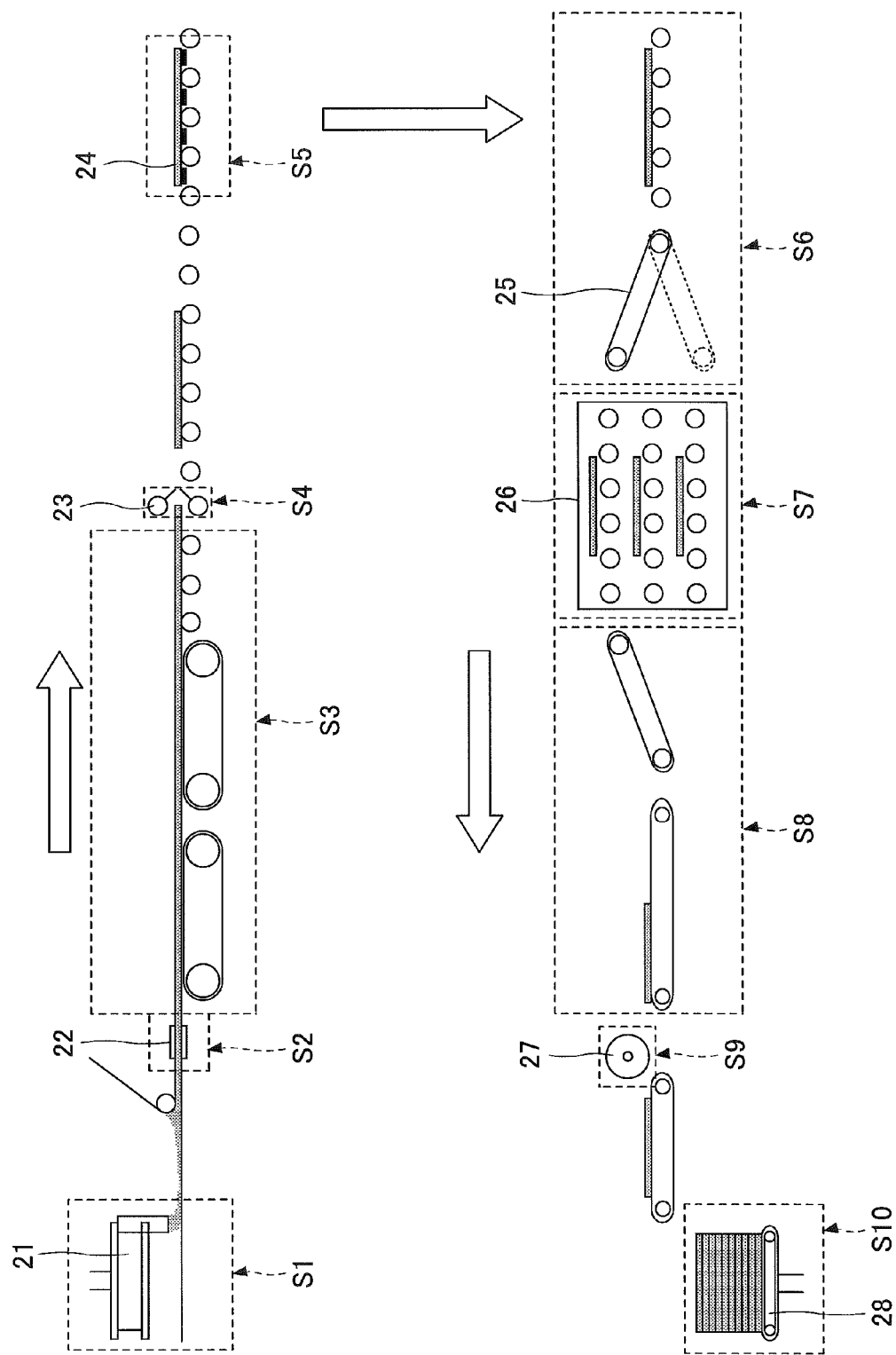
FIG. 2 is a schematic diagram illustrating a method of manufacturing a gypsum-based building board according to a second embodiment of the present invention.

A description is given, with reference to FIG. 2 and FIG. 3, of a method of manufacturing a gypsum-based building board. FIG. 2 is a schematic diagram illustrating a method of manufacturing a gypsum-based building board from a side. FIG. 3 is a flowchart of the method of manufacturing a gypsum-based building board illustrated in FIG. 2.

In a mixture and agitation process of step S1, as described in the first embodiment, calcined gypsum and water, and an adhesive agent and other various kinds of additives as required, are agitated and mixed in a mixer agitator (main mixer) 21, so that a homogeneous gypsum slurry for a gypsum-based building board is obtained.

The specific components of the gypsum slurry are as described in the first embodiment, and their description is therefore omitted.

Next, in a forming process of step S2, the gypsum slurry and, for example, cover paper, glass mats, and/or glass fiber tissues are formed into a predetermined shape with a forming machine 22.

For example, in the case of manufacturing a gypsum board, the gypsum board is formed by depositing the gypsum slurry on an upper surface of continuously conveyed lower paper (cover paper), placing upper paper (cover paper) conveyed at the same speed as the lower paper on this layer of the gypsum slurry while folding the lower paper along scores marked one on each end edge portion of the lower paper so as to wrap up the gypsum slurry, and causing the gypsum slurry covered with the upper and the lower paper to pass through the forming machine 22 that determines the thickness and the width of the gypsum board.

Then, in a first conveyance process of step S3, the formed gypsum-based building board is conveyed on a belt conveyor or conveyor rollers to a rough cutter (a rotary cutter)

23 in a rough cutting process of step S4, where the conveyed gypsum-based building board is roughly cut.

Thereafter, in a drying process of step S7, the gypsum-based building board is conveyed into a drying machine (dryer) 26 and is subjected to forced drying. Depending on the layout of the arrangement or the like, for example, a process for turning the board upside down with an inverting machine (inverter) 24 (a turnover process of step S5) and/or a process for conveying the board with conveyor rollers or a conveyor belt 25 (a second conveyance process of step S6) may be interposed between the rough cutter (rotary cutter) 23 of the rough cutting process and the drying machine (dryer) 26 as illustrated in FIG. 2.

Then, in a third conveyance process of step S8, the dried gypsum-based building board is conveyed to a cutter (sizer) 27, and in a cutting process of step S9, the dried gypsum-based building board is cut to a product size with the cutter (sizer) 27. In a loading process of step S10, a predetermined number of cut gypsum-based building boards are orderly piled and stored in a warehouse by a lifter 28.

The manufacturing process described here illustrates an overview of the method of manufacturing a gypsum-based building board, and the method of manufacturing a gypsum-based building board is not limited to this form. Depending on the layout of the arrangement, the form of a gypsum-based building board to be manufactured, etc., a process may be, for example, changed, added, and/or omitted.

The method of detecting an air gap in a gypsum-based building board described in the first embodiment is applied in this manufacturing process.

In this case, the cooling process of applying a cooling medium to a surface of the gypsum-based building board that has generated heat because of a hydration reaction and thereby cooling the surface may be performed at any time during the heat generation of the gypsum-based building board due to the hydration reaction (due to the hydration reaction of calcined gypsum).

In a common manufacturing method of a gypsum-based building board, the hydration reaction of calcined gypsum starts after the mixture and agitation process (step S1) for mixing calcined gypsum, water, etc., and the hydration reaction is completed before the drying process (step S7) is performed. Therefore, it is possible to perform the cooling process between the forming process (step S2) and the second conveyance process (step S6).

In order to prevent deformation of the gypsum-based building board at the time of application of a cooling medium to the board, it is preferable to apply a cooling medium during conveyance of the gypsum-based building board with a belt conveyor or conveyor rollers. Therefore, in the case of the above-described manufacturing process, it is more preferable to perform the cooling process in either the first conveyance process (step S3) or the second conveyance process (step S6), for example.

After the rough cutting process is performed, the gypsum-based building board is divided into multiple boards. Therefore, it is necessary to perform the cooling process and the subsequent temperature distribution detection process with respect to each of the cut boards, which complicates the process. Furthermore, if it is possible to discover an air gap inside the gypsum-based building board on the upstream side in the manufacturing process, it is possible to reduce time taken before changing manufacturing conditions after generation of a defective product. As a result, it is possible to reduce the rate of generation of defective products and to improve the product yield.

Therefore, it is more preferable to perform the cooling process between the forming process (step S2) and the rough cutting process (step S4). Furthermore, the cooling process is performed by applying a cooling medium to the gypsum-based building board for a certain time. Therefore, in the case of the above-described manufacturing process, it is particularly preferable to perform the cooling process in the first conveyance process (step S3) in terms of its workability.

Furthermore, the temperature distribution detection process of detecting the temperature distribution of a surface of the gypsum-based building board may be performed at any time while the temperature difference is such as to allow a part containing an air gap and other parts of the gypsum-based building board to be distinguished after the cooling process as described above.

For example, like the cooling process, the temperature distribution detection process may be performed between the forming process (step S2) and the second conveyance process (step S6). In this case, it is easy to detect the temperature distribution of a surface of the gypsum-based building board when the gypsum-based building board is conveyed with a belt conveyor or conveyor rollers. Therefore, it is more preferable to perform the temperature distribution detection process in either the first conveyance process (step S3) or the second conveyance process (step S6).

Like in the case of the cooling process, it is preferable to be able to detect an air gap inside the gypsum-based building board on the upstream side in the manufacturing process. Therefore, it is more preferable to perform the temperature distribution detection process between the forming process (step S2) and the rough cutting process (step S4). Furthermore, because it is easy to detect the temperature distribution of a surface of the gypsum-based building board when the gypsum-based building board is conveyed with a belt conveyor or conveyor rollers, it is particularly preferable to perform the temperature distribution detection process in the first conveyance process (step S3).

In the manufacturing process of the gypsum-based building board, when the gypsum-based building board is continuously conveyed, parts of the gypsum-based building board that have been subjected to the cooling process may be subjected to the temperature distribution detection process one after another at predetermined intervals.

Furthermore, as described in the first embodiment as well, it is preferable to further include the temperature distribution imaging process of imaging the temperature distribution of a surface of the gypsum-based building board obtained in the temperature distribution detection process and the air gap size detection process of detecting the size of an air gap contained in the gypsum-based building board by performing image processing on the image of the temperature distribution of a surface of the gypsum-based building board obtained in the temperature distribution imaging process.

It is preferable to apply the method of manufacturing a gypsum-based building board of this embodiment in the case of continuously manufacturing gypsum-based building boards in a factory or the like. It is preferable in terms of efficiency to automatically detect the size of an air gap inside the gypsum-based building board by image processing in the continuous manufacturing.

Furthermore, this configuration makes it possible to detect the size of an air gap with more accuracy.

In the air gap size detection process, there is no need to detect the size of an air gap with respect to all regions of a different temperature in the temperature distribution (regions corresponding to air gaps). The size of an air gap may be detected with respect to a region of a different temperature in the temperature distribution (a region corresponding to an air gap) required to be detected that is larger than or equal to a predetermined certain size.

For example, as described below, in the case where it is desired to detect an air gap larger than or equal to a size allowable for a product (a product allowable size) and take action, the size of a region of a different temperature in the temperature distribution (a region corresponding to an air gap) to be subjected to an operation may be selected in view of detection accuracy, etc., so that every air gap of a target size may be detected.

Furthermore, it is preferable that when an air gap larger than or equal to the product allowable size is detected in the air gap size detection process, part of the gypsum-based building board that contains the air gap be determined as a defective piece and ejected outside the system of the manufacturing line of the gypsum-based building board.

It is preferable to have a configuration that, when an air gap larger than or equal to a (predetermined) product allowable size is detected, ejects part of the gypsum-based building board that contains the air gap outside the system as described above because this makes it possible to automatically reject a gypsum-based building board that does not satisfy product specifications.

The process of ejecting a defective product may be so configured as to allow ejection of part of the gypsum-based building board that contains a detected air gap after the air gap size detecting process, and may be performed in any of the processes.

For example, the defective product ejection process may be performed between the cutting process (step S9) and the loading process (step S10). It is also possible to perform the defective product ejection process between the rough cutting process (step S4) and the loading process (step S10) when the air gap size detection process is completed before the rough cutting process (step S4).

The air gap larger than or equal to a product allowable size referred to here is selected (determined) in accordance with the specifications of individual gypsum-based building boards or the like and is not limited. For example, the air gap larger than or equal to a product allowable size is preferably an air gap larger than or equal to 20 mm in diameter, more preferably an air gap larger than or equal to 15 mm in diameter, and still more preferably an air gap larger than or equal to 10 mm in diameter.

When the shape of an air gap is, for example, an ellipsoid like a hen's egg, the diameter of an air gap referred to here means the length of the longest portion in a longitudinal direction in its cross section.

It is possible to ensure prevention of shipment of a defective product by thus detecting part of the gypsum-based building board that contains an air gap, distinguishing between non-defective and defective pieces based on the size of an air gap, the number of air gaps or the like, and automatically marking and ejecting outside the system a product that contains an air gap and is determined as being defective.

Furthermore, in the above-described air gap size detection process, it is preferable to issue an alarm that prompts a change in manufacturing conditions when an air gap is detected that is larger than or equal to a size that requires a change in manufacturing conditions.

Air gaps are generated because of manufacturing conditions or the like. Therefore, if the manufacturing continues under the same conditions, air gaps are expected to be likewise contained in gypsum-based building boards to be manufactured. Therefore, by issuing an alarm and causing a change in manufacturing conditions at an early stage in response to detecting an air gap larger than or equal to a predetermined certain size, it is possible to reduce the rate of generation of defective products.

The air gap larger than or equal to a size that requires a change in manufacturing conditions referred to here is selected (determined) in accordance with the specifications of the gypsum-based building board that are required, and is not limited in particular. For example, the air gap larger than or equal to a size that requires a change in manufacturing conditions is preferably an air gap larger than or equal to 20 mm in diameter, more preferably an air gap larger than or equal to 15 mm in diameter, and still more preferably an air gap larger than or equal to 10 mm in diameter.

The alarm that prompts a change in manufacturing conditions is not limited in particular as long as the alarm is recognizable by a controller of the manufacturing arrangement. The alarm may be issued by way of, for example, a buzzer, indicator light, display on a computer screen for the controller, or the like.

It is satisfactory to only prompt the controller of the manufacturing arrangement to make a change in manufacturing conditions by the above-described display or the like. It is also possible, however, to, for example, automatically select optimum manufacturing conditions from the manufacturing conditions registered with a database in accordance with the detected size of an air gap, the number of generated air gaps or the like, and present the selected optimum manufacturing conditions on the screen, and to prompt a change to the presented manufacturing conditions.

The specific contents of a change in manufacturing conditions for preventing generation of air gaps are not limited in particular. For example, a percentage of water mixture (a ratio of water to calcined gypsum), the added amount of a dispersant, the consistency of a gypsum slurry, the rate of manufacturing, etc., may be changed. Furthermore, the rotation speed or the like of a vibrator that removes air inside a gypsum slurry by vibrating the gypsum slurry may be adjusted. These changes and adjustment may be made independently or two or more of them may be made in combination.

Thus, according to the method of manufacturing a gypsum-based building board of this embodiment, it is possible to determine the presence or absence of an air gap and detect the size of an air gap earlier than the drying process of step S7 after passing through the forming machine 22. This makes it possible to quickly provide feedback concerning the manufacturing conditions and accordingly to reduce the generation of defective products.

According to the method of manufacturing a gypsum-based building board of this embodiment as has been described, heat generation due to the heat of hydration (of the calcined gypsum) of a product (a gypsum-based building board) is used in detecting an air gap inside the product. This makes it possible to omit equipment and energy for newly applying heat. Furthermore, a temperature difference is caused by simply cooling a surface of the product with a cooling medium. The temperature difference is more distinct because of continuing heat generation of the product than a temperature difference caused by cooling alone, thus facilitating detection of an air gap inside the product.

Furthermore, in the case of applying the method of detecting an air gap in a gypsum-based building board according to the first embodiment to the upstream part of a process for manufacturing a gypsum-based building board as described above, even when a defective product that contains an air gap larger than or equal to a predetermined size is generated, it is possible to detect the defective product and provide feedback concerning the manufacturing conditions at an early stage, so that it is possible to reduce the number of defective products and to improve a yield.

EXAMPLES

A description is given below of specific examples and comparative examples. The present invention, however, is not limited to these examples.

Example 1

Gypsum boards of 12.5 mm in thickness were continuously manufactured at a manufacturing rate of 150 m/min. in accordance with the gypsum board manufacturing process illustrated in FIG. 2 and FIG. 3.

First, the mixture and agitation process (step S1) was performed to manufacture a gypsum slurry by agitating and mixing calcined gypsum, water, and an adhesive agent with the mixer agitator (main mixer) 21.

Then, the forming process (step S2) was performed to deposit the gypsum slurry on an upper surface of continuously conveyed lower paper (cover paper), place upper paper (cover paper) conveyed at the same speed as the lower paper on this layer of the gypsum slurry while folding the lower paper along scores marked one on each end edge portion of the lower paper so as to wrap up the gypsum slurry, and form the gypsum slurry covered with the upper and the lower paper in the forming machine 22 so that gypsum board products were 12.5 mm in thickness and 910 mm in width.

Thereafter, the first conveyance process (step S3) to convey a formed gypsum board on a belt conveyor or conveyor rollers to the rough cutter (rotary cutter) 23 of the rough cutting process (step S4) and the rough cutting process (step S4) to roughly cut the formed gypsum board with the rough cutter (rotary cutter) 23 were performed.

Thereafter, the turnover process (step S5) to turn the gypsum board upside down with the inverting machine (inverter) 24, the second conveyor process (step S6) to convey the gypsum board with conveyor rollers or the conveyor belt 25 into the drying machine (dryer) 26, and the drying process (step S7) to subject the gypsum board conveyed into the drying machine (dryer) 26 to forced drying were performed.

Then, the third conveying process (step S8) to convey the dried gypsum board with a conveyor belt or the like to the cutter (sizer) 27 was performed, and thereafter, the cutting process (step S9) to cut the gypsum board to a product size with the cutter (sizer) 27 was performed.

In the loading process (step S10), a predetermined number of cut gypsum boards were orderly piled and stored in a warehouse by the lifter 28.

In this example, the cooling process of cooling a surface of the gypsum board by applying a wind to the entire surface of the gypsum board using two blowers of 2.2 kW and 3.7 kW, the temperature distribution detection process of detecting the temperature distribution of a surface of the gypsum board by thermography, and the temperature distribution imaging process of imaging the temperature distribution obtained in the temperature distribution detection process were performed in the first conveyance process (step S3).

At this point, because of the cooling process and heat generation due to the hydration reaction of the calcined gypsum, the surface temperature of part of the gypsum board containing no air gap was approximately 45° C. and the surface temperature of part of the gypsum board containing an air gap was approximately 42° C.

Then, the air gap size detection process of detecting the size of an air gap contained in the gypsum board by performing image processing on the image of the temperature distribution of a surface of the gypsum board obtained in the temperature distribution imaging process was performed, so that air gaps were automatically detected.

Furthermore, the air gap size detection process was configured so as to mark a product and eject the product outside the system of the manufacturing line, and to notify a controller of an alarm to prompt a change in manufacturing conditions when an air gap of 15 mm or larger in diameter was discovered.

Under these conditions, time was measured from when the operation of a vibrator, which removes air inside the gypsum slurry between the mixer agitator (main mixer) 21 and the forming machine 22, was stopped so as to cause mixture of large air bubbles, which are the cause of air gaps, into the gypsum slurry in the forming process (step S2), to when an air gap of 15 mm or larger was detected in the air gap size detection process.

As a result, in this example, it was possible to detect an air gap of 15 mm or larger in diameter in approximately 4 minutes after the stoppage of the operation of the vibrator. The smallest size of the air gaps detected at this time was 3 mm in diameter.

In addition, an air gap of 15 mm or larger in diameter was marked and a corresponding part of the gypsum board was ejected outside the manufacturing line after the cutting process (step S9). Furthermore, with the detection of the air gap, a controller of the manufacturing process was notified of an alarm to prompt a change in manufacturing conditions, and it was possible to start the operation of the vibrator based on this notification.

Example 2

Gypsum boards containing glass fiber tissues were manufactured at a manufacturing rate of 15 m/min. with substantially the same manufacturing equipment as in Example 1 except that glass fiber tissues were used in place of cover paper and a gypsum board containing glass fiber tissues of 9.5 mm in thickness was formed in the forming process in order to manufacture gypsum boards containing glass fiber tissues.

In this case, an air gap of 15 mm or larger was detected in the air gap size detection step in 9 minutes after the operation of the vibrator, which removes air inside the gypsum slurry, was stopped. The smallest size of the air gaps detected at this time was 3 mm in diameter.

In addition, an air gap of 15 mm or larger in diameter was marked and a corresponding part of the gypsum board containing glass fiber tissues was ejected outside the manufacturing line after the cutting process (step S9). Furthermore, with the detection of the air gap, a controller of the manufacturing process was notified of an alarm to prompt a change in manufacturing conditions, and it was possible to start the operation of the vibrator based on this notification.

Comparative Example 1

In this comparative example, the manufacturing process was performed the same as in Example 1 except that the processes for detecting an air gap in the gypsum board (the cooling process, the temperature distribution detection process, the temperature distribution imaging process, and air gap size detection process) were not performed in the first conveyance process (step S3) and that the following air gap detection process was performed in the third conveyance process (step S8).

A description is given of the air gap detection process.

In the third conveyance process (step S8), while the hydration reaction has already ended, the entire surface of the gypsum board is uniformly heated by the drying machine (dryer) 26 of the drying process (step S7).

Thereafter, like in the case of Example 1, the cooling process of cooling a surface of the gypsum board by applying a wind to the entire surface of the gypsum board using two blowers of 2.2 kW and 3.7 kW was performed. This is because a difference in the degree of cooling is caused between a part containing an air gap and other parts of the gypsum board so that a temperature distribution is obtained.

Next, the temperature distribution detection process of detecting the temperature distribution of a surface of the gypsum board by thermography and the temperature distribution imaging process of imaging the temperature distribution obtained in the temperature distribution detection process were performed.

Then, the air gap size detection process of detecting the size of an air gap contained in the gypsum board by performing image processing on the image of the temperature distribution of a surface of the gypsum board obtained in the temperature distribution imaging process was performed, so that an air gap of 15 mm or larger in diameter was detected.

In this case, the air gap was detected in 56 minutes after the operation of the vibrator was stopped.

In this comparative example, compared with the result of Example 1, the detection of the air gap is 52 minutes late, and the change of manufacturing conditions (the restart of the operation of the vibrator) is also equally late.

In this comparative example, the number of gypsum boards manufactured before the detection of the air gap after the time of detection in Example 1 (a time point of 4 minutes) was approximately 4280 (1820 mm in length per product). In these gypsum boards, defective products are present at least in a certain proportion. Therefore, compared with the case of Example 1, the productivity and yield are significantly reduced.

Comparative Example 2

In this comparative example, the manufacturing process was performed the same as in Example 2 except that the processes for detecting an air gap in the gypsum board containing glass fiber tissues (the cooling process, the temperature distribution detection process, the temperature distribution imaging process, and air gap size detection process) were not performed in the first conveyance process (step S3) and that the following air gap detection process was performed in the third conveyance process (step S8).

In the third conveyance process (step S8), while the hydration reaction has already ended, the entire surface of the gypsum board containing glass fiber tissues is uniformly heated by the drying machine (dryer) 26 of the drying process (step S7).

Thereafter, like in the case of Example 2, the cooling process of cooling a surface of the gypsum board containing glass fiber tissues by applying a wind to the entire surface of the gypsum board containing glass fiber tissues using two blowers of 2.2 kW and 3.7 kW was performed.

This is because a difference in the degree of cooling is caused between a part containing an air gap and other parts of the gypsum board so that a temperature distribution is obtained.

Next, the temperature distribution detection process of detecting the temperature distribution of a surface of the gypsum board containing glass fiber tissues by thermography and the temperature distribution imaging process of imaging the temperature distribution obtained in the temperature distribution detection process were performed.

Then, the air gap size detection process of detecting the size of an air gap contained in the gypsum board containing glass fiber tissues by performing image processing on the image of the temperature distribution of a surface of the gypsum board containing glass fiber tissues obtained in the temperature distribution imaging process was performed, so that an air gap of 15 mm or larger in diameter was detected.

In this case, the air gap was detected in 227 minutes after the operation of the vibrator was stopped.

Compared with the result of Example 2, the detection of the air gap is 218 minutes late, and the change of manufacturing conditions (the restart of the operation of the vibrator) is also equally late.

In this comparative example, the number of gypsum boards manufactured before the detection of the air gap after the time of detection in Example 2 (a time point of 9 minutes) was approximately 1790 (1820 mm in length per product). In these gypsum boards, defective products are present at least in a certain proportion. Therefore, compared with the case of Example 2, the productivity and yield are significantly reduced.

All examples and conditional language provided herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority or inferiority of the invention. Although one or more embodiments of the present invention have been described in detail, it should be understood that the various changes, substitutions, and alterations could be made hereto without departing from the spirit and scope of the invention.

This application is based upon and claims the benefit of priority of Japanese Patent Application No. 2012-230499, filed on Oct. 18, 2012, the entire contents of which are incorporated herein by reference.

The invention claimed is:

1. A method of manufacturing a gypsum-based building board, comprising:
    forming the gypsum-based building board of a predetermined shape;
    cooling a surface of the gypsum-based building board that has generated heat because of a hydration reaction of calcined gypsum by applying a cooling medium to the surface;
    detecting a temperature distribution of the surface of the gypsum-based building board after completion of said cooling;
    imaging the temperature distribution obtained in said detecting;
    automatically detecting an air gap larger than or equal to a predetermined size contained in the gypsum-based building board by performing image processing on an image of the temperature distribution of the surface of the gypsum-based building board obtained in said imaging; and determining a part of the gypsum-based building board that contains the air gap as being defective, and automatically marking the part and ejecting the part outside a system of a manufacturing process.

2. The method of manufacturing the gypsum-based building board as claimed in claim 1, further comprising:

issuing an alarm to prompt a change in a manufacturing condition and prompting the change in at least one of manufacturing conditions of a ratio of water to the calcined gypsum, an added amount of a dispersant, a consistency of a gypsum slurry, a rate of manufacturing, and a rotation speed of a vibrator that vibrates the gypsum slurry, when the air gap larger than or equal to the predetermined size is detected.

3. The method of manufacturing the gypsum-based building board as claimed in claim 1, further comprising:

issuing an alarm to prompt a change in a manufacturing condition, and automatically selecting an optimum manufacturing condition from manufacturing conditions registered with a database and prompting the change to the selected manufacturing condition, when the air gap larger than or equal to the predetermined size is detected.

* * * * *